(12) United States Patent
Pincus

(10) Patent No.: US 7,745,405 B2
(45) Date of Patent: *Jun. 29, 2010

(54) PEPTIDES SELECTIVELY LETHAL TO MALIGNANT AND TRANSFORMED MAMMALIAN CELLS

(75) Inventor: Matthew R. Pincus, Brooklyn, NY (US)

(73) Assignee: The Research Foundation of State University of New York, Albany, NY (US)

( * ) Notice: Subject to any disclaimer, the term of this patent is extended or adjusted under 35 U.S.C. 154(b) by 79 days.

This patent is subject to a terminal disclaimer.

(21) Appl. No.: 11/977,521

(22) Filed: Oct. 25, 2007

(65) Prior Publication Data

US 2008/0076713 A1 Mar. 27, 2008

Related U.S. Application Data

(63) Continuation of application No. 11/582,687, filed on Oct. 17, 2006, now Pat. No. 7,531,515, which is a continuation of application No. 10/386,737, filed on Mar. 12, 2003, now abandoned, which is a continuation-in-part of application No. 09/827,683, filed on Apr. 5, 2001, now abandoned.

(60) Provisional application No. 60/363,785, filed on Mar. 12, 2002, provisional application No. 60/195,102, filed on Apr. 5, 2000.

(51) Int. Cl.
*A61K 38/00* (2006.01)
*C07K 5/00* (2006.01)

(52) U.S. Cl. .............................. 514/12; 514/15; 514/14; 530/324; 530/327; 530/328

(58) Field of Classification Search ....................... None
See application file for complete search history.

(56) References Cited

U.S. PATENT DOCUMENTS

| 4,215,102 A | 7/1980 | Lee |
| 5,369,012 A | 11/1994 | Koontz et al. |
| 5,770,377 A | 6/1998 | Picksley et al. |

FOREIGN PATENT DOCUMENTS

| WO | 96/02642 A | 2/1996 |
| WO | 98/01467 | 1/1998 |
| WO | 98/47919 | 10/1998 |
| WO | 2004/081030 | 9/2004 |

OTHER PUBLICATIONS

Kanovsky et al., (2001) "Peptides from the amino terminal mdm-2-binding domain of p53, designed from conformational analysis, are selectively cytotoxic to transformed cells", *PNAS*, 98, No. 2, pp. 12438-12443.
Wasylyk, Christine, et al., (1999) "p53 mediated death of cells overexpressing MDM2 by an inhibitor of MDM2 interaction with p53", *Oncogene*, 18:1921-34.
Lin et al. (1975) *Biochemistry* 14, p. 1559.
Burgess et al., (1990) *Journal of Cell Biology* 111, p. 2129-2138.
Scheller et al., (2000) *Eur J Biochem* 267, p. 6043.
Futaki et al. (2001) *J. Biol. Chem.* 276 p. 5836.
Elmquist et al. (2001) *Experimental Cell Research* 269 p. 237.

*Primary Examiner*—Sheela J Huff
(74) *Attorney, Agent, or Firm*—Dilworth & Barrese, LLP

(57) ABSTRACT

The present invention provides peptides corresponding to all or a portion of amino acid residues 12-26 of human p53 protein. When fused to a membrane-penetrating leader sequence, the peptides are either lethal to malignant or transformed cells or else cause reversion to the untransformed morphological phenotype. The subject peptides are thus useful in treating neoplastic disease in an animal, preferably a human. Also provided are pharmaceutical compositions comprising the subject peptides admixed with a pharmaceutical acceptable carrier. Methods of treating neoplastic disease in a patient by administering a subject peptide are also provided.

13 Claims, 1 Drawing Sheet

PEPTIDES SELECTIVELY LETHAL TO MALIGNANT AND TRANSFORMED MAMMALIAN CELLS

This application is a continuation of application Ser. No. 11/582,687, filed Oct. 17, 2006, now U.S. Pat. No. 7,531,515 which is a continuation of application Ser. No. 10/386,737, filed Mar. 12, 2003, now abandoned, which is a continuation-in-part application of application Ser. No. 09/827,683, filed Apr. 5, 2001, now abandoned, this application claims the benefit of U.S. Provisional Application No. 60/363,785, filed Mar. 12, 2002, and U.S. Ser. No. 09/827,683 claims the benefit of U.S. Provisional Application Ser. No. 60/195,102, filed Apr. 5, 2000.

BACKGROUND OF THE INVENTION

This invention relates to therapeutic modalities for treatment of neoplastic disease. More specifically, this invention involves synthetic peptides that selectively destroy malignant and transformed cells, and a method for treatment of neoplastic disease based thereon.

The p53 protein is a vital regulator of the cell cycle. It blocks the oncogenic effects of a number of oncogene proteins that induce mitosis, in part by blocking transcription of proteins that induce mitosis and by inducing the transcription of proteins that block mitosis, and promote apoptosis. Absence of the p53 protein is associated with cell transformation and malignant disease. Haffner, R & Oren, M. (1995) Curr. Opin. Genet. Dev. 5: 84-90.

The p53 protein molecule consists of 393 amino acids. It includes domains that bind to specific sequences of DNA in a DNA-binding domain that consists of residues 93-313. The crystal structure of this region has been determined by x-ray crystallography. Residues 312-393 are involved in the formation of homotetramers of the p53 protein. Residues 1-93 are involved in regulation of the activity and half life of the p53 protein.

The p53 protein binds to another important regulatory protein, the MDM-2 protein. The MDM-gene that encodes the MDM-2 protein is a known oncogene. The MDM-2 protein forms a complex with the p53 protein, which results in the degradation of the p53 protein by a ubiquination pathway. The p53 protein binds to MDM-2 protein using an amino acid sequence that includes residues 14-22 of the p53 protein, which are invariant. The entire MDM-2 protein binding domain of the p53 protein spans residues 12-26. Haffner, R & Oren, M. (1995) Curr. Opin. Genet. Dev. 5: 84-90.

Considering that the MDM-2 protein is the expression product of a known oncogene, it is not surprising that MDM-2 protein is a very important regulatory protein. Moreover, overexpression or amplification of MDM-2 protein has been found in 40-60% of human malignancies, including 50% of human breast tumors. It has been suggested that formation of a complex between the p53 protein and the MDM-2 protein may result in the inhibition of transcription activity of the p53 protein, and thus the anti-tumor effect of the molecule by blocking of an activation domain of the p53 protein, or of a DNA binding site within it. More generally, these and other experimental observations have been interpreted as suggesting that the anti-tumor effect of the p53 protein might be enhanced by peptides capable of interfering with the binding of the MDM-2 protein to the p53 protein. Indeed, a number of investigators have suggested that the MDM-2/p53 complex might be a target for rational drug design. See, e.g., Christine Wasylyk et al., "p53 Mediated Death of Cells Overexpressing MDM2 by an Inhibitor of MDM2 Interaction with p53", Oncogene, 18, 1921-34 (1999), and U.S. Pat. No. 5,770,377 to Picksley et al.

SUMMARY OF THE INVENTION

The present invention provides a peptide comprising at least about six contiguous amino acids of the amino acid sequence: PPLSQETFSDLWKLL (SEQ ID NO:1), or an analog or derivative thereof, wherein said peptide or analog or derivative thereof is fused to a membrane-penetrating leader sequence and is selectively lethal to malignant or transformed cells.

Examples of such peptides include PPLSQETFSDLWKLL (SEQ ID NO:1) or an analog or derivative thereof, PPLSQETFS (SEQ ID NO:2) or an analog or derivative thereof and ETFSDLWKLL (SEQ ID NO:3) or an analog or derivative thereof. In order to be transported across a cell membrane and selectively kill a malignant or transformed cell, the leader sequence is preferably positioned at the carboxyl terminal end of the peptide, analog, or derivative thereof. Preferably, the leader sequence comprises predominantly positively charged amino acid residues. Examples of leader sequences which may be used in accordance with the present invention include but are not limited to penetratin, $Arg_8$, TAT of HIV1, D-TAT, R-TAT, SV40-NLS, nucleoplasmin-NLS, HIV REV (34-50), FHV coat (35-49), BMV GAG (7-25), HTLV-II REX (4-16), CCMV GAG (7-25), P22N (14-30), Lambda N (1-22), Delta N (12-29), yeast PRP6, human U2AF, human C-FOS (139-164), human C-JUN (252-279), yeast GCN4, and p-vec. Preferably, the leader sequence is the penetratin sequence from antennapedia protein having the amino acid sequence KKWKMRRNQFWVKVQRG (SEQ ID NO:4).

Pharmaceutical compositions comprising at least one of the subject peptides admixed with a pharmaceutically acceptable carrier are also provided. In addition, methods for treating neoplastic disease in a subject i.e., selectively killing malignant or neoplastic cells in a subject, are provided. In one embodiment, the method comprises administering to the subject, a therapeutically effective amount of a peptide comprising at least about six contiguous amino acids of the amino acid sequence: PPLSQETFSDLWKLL (SEQ ID NO:1), or an analog or derivative thereof, wherein said peptide or analog or derivative thereof is fused at its carboxy terminal end to a membrane-penetrating leader sequence and is selectively lethal to malignant or transformed cells. In another embodiment, the method comprises administering to the subject, a therapeutically effective amount of at least one peptide having the sequence set forth in SEQ ID NO:1, SEQ ID NO:2, or SEQ ID NO:3, or an analog or derivative thereof, wherein a membrane-penetrating leader sequence is fused to the carboxy terminal end of the peptide, analog, or derivative thereof.

DETAILED DESCRIPTION OF THE INVENTION

Figure 1:
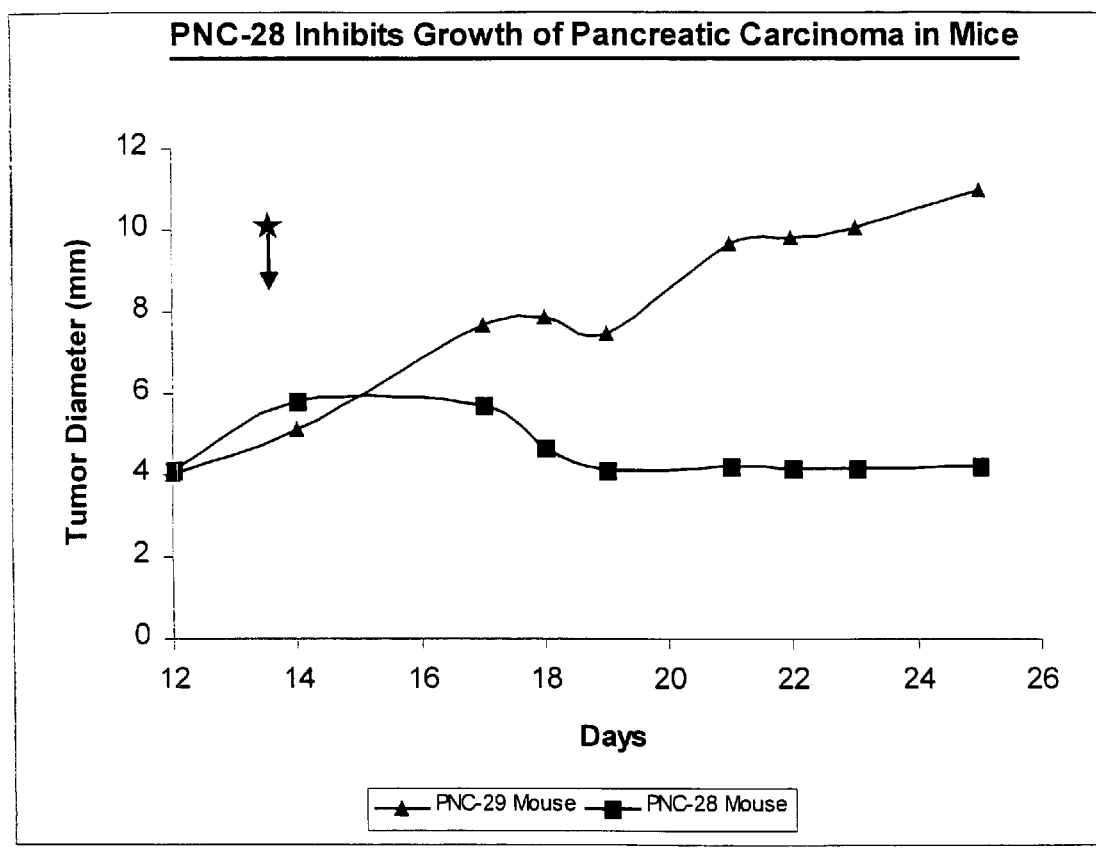
FIG. 1 graphically depicts the in vivo tumor-inhibiting effect of PNC-28 (SEQ ID NO:3 fused at its carboxy terminal end to SEQ ID NO:4) in homozygous NU/NU mice xenotransplanted with pancreatic carcinoma cells. The arrow with a star indicates the time of s.c. pump implantation on day 13 (precisely 13.5) during the tumor growth period.

In accordance with the present invention, it has been discovered that malignant and transformed cells are selectively destroyed by administration of a synthetic peptide comprising a sequence of amino acids within the p53 protein and a leader sequence as a single continuous polypeptide chain. The mechanism of action appears to be independent of the p53 protein binding to the MDM-2 protein, as the p53 peptide selectively kills transformed cells that do not produce the p53 protein at all. The p53 peptide also selectively kills malignant and transformed cells that express normal or elevated levels of the p53 protein without killing normal cells.

In accordance with the present invention, there are provided compositions comprising peptides corresponding to all or a portion of amino acid residues 12-26 of human p53. This region is known to contact the mdm-2 protein and adopts an α-helical conformation when bound to mdm-2. When fused on the carboxy-terminal end with a membrane-penetrating leader sequence, the subject peptides selectively kill malignant and transformed human cells.

In a first aspect of the invention, there is provided a peptide comprising at least about six contiguous amino acids of the following amino acid sequence: PPLSQETFSDLWKLL (SEQ ID NO:1), wherein the peptide comprising at least about six contiguous amino acids is fused to a leader sequence. Preferably, the peptide comprises from at least about eight (8) to at least about fifteen (15) amino acid residues. In a preferred embodiment, a peptide comprising from at least about eight (8) to at least about 15 (fifteen) amino acids of the sequence set forth in SEQ ID NO:1 has the following amino acid sequence: PPLSQETFSDLWKLL (SEQ ID NO:1). In another preferred embodiment, a peptide comprising from at least about eight (8) to at least about 15 (fifteen) amino acids of the sequence set forth in SEQ ID NO:1 has the following amino acid sequence: PPLSQETFS (SEQ ID NO:2). In still another preferred embodiment, a peptide comprising from at least about eight (8) to at least about fifteen (15) amino acids of the sequence set forth in SEQ ID NO:1 has the following amino acid sequence: ETFSDLWKLL (SEQ ID NO:3).

Leader sequences which function to import the peptides of the invention into a cell may be derived from a variety of sources. Preferably, the leader sequence comprises predominantly positively charged amino acid residues since a positively charged leader sequence stabilizes the alpha helix of a subject peptide. Examples of leader sequences which may be linked to the peptides of the present invention are described in Futaki, S. et al (2001) Arginine-Rich Peptides, *J. Biol. Chem.* 276:5836-5840, and include but are not limited to the following membrane-penetrating leader sequences (numbering of the amino acid residues making up the leader sequence of the protein is indicated parenthetically immediately after the name of the protein in many cases): penetratin (KKWKMRRNQFWVKVQRG) (SEQ ID NO:4); (Arg)$_8$ (SEQ ID NO:26) or any poly-R from (R)$_4$-(R)$_{16}$ (SEQ ID NO:27); HIV-1 TAT(47-60) (YGRKKRRQRRRPPQ) (SEQ ID NO:5); D-TAT (GRKKRRQRRRPPQ) (SEQ ID NO:6); R-TAT G(R)$_9$PPQ (SEQ ID NO:7); SV40-NLS (PKKKRKV) (SEQ ID NO:8); nucleoplasmin-NLS (KRPAAIKKAGQAKKKK) (SEQ ID NO:9); HIV REV (34-50)-(TRQARRNRRRRWRERQR) ID NO:10); FHV (35-49) coat-(RRRRNRTRRNRRRVR) (SEQ ID NO:11); BMV GAG (7-25)-(KMTRAQRRAAARRNRWTAR) (SEQ ID NO:12); HTLV-II REX 4-16-(TRRQRTRRARRNR) (SEQ ID NO:13); CCMV GAG (7-25)-(KLTRAQRRAAARKNKRNTR) (SEQ ID NO:14); P22 N (14-30)(NAKTRRHERRRKLAIER) (SEQ ID NO:15); LAMBDA N (1-22)(MDAQTRRRERRAEKQAQWKAAN) (SEQ ID NO:16); Phi N (12-29) (TAKTRYKARRAELIAERR) (SEQ ID NO:17); YEAST PRP6 (129-124) (TRRNKRNRIQEQLNRK) (SEQ ID NO:18); HUMAN U2AF (SQMTRQARRLYV) (SEQ ID NO:19); HUMAN C-FOS (139-164) KRRIRRERNKMAAAKSRNRRRELTDT (SEQ ID NO:20); HUMAN C-JUN (252-279) (RIKAERKRMRNRIAASKSRKRKLERIAR) (SEQ ID NO:21); YEAST GCN4 (KRARNTEAARRSRARKLQRMKQ) (SEQ ID NO:22); KLALKLALKALKAALKLA (SEQ ID NO:23); p-vec LLI-ILRRRIRKQAKAHSK (SEQ ID NO:24). Other membrane penetrating leader sequences may also be used. Such sequences are widely available and are described e.g., in Scheller et al. (2000) *Eur. J. Biochem.* 267:6043-6049, and Elmquist et al., (2001) *Exp. Cell Res.* 269:237-244.

Preferably, the positively charged leader sequence of the penetratin leader sequence of antennapedia protein is used. This leader sequence has the following amino acid sequence: KKWKMRRNQFWVKVQRG (SEQ ID NO:4). Preferably, the leader sequence is attached to the carboxyl terminal end of the p53 peptide to enable the synthetic peptide to kill transformed and malignant cells.

Structurally related amino acid sequences may be substituted for the disclosed sequences set forth in SEQ ID NOs: 1, 2, 3, or 4 in practicing the present invention. Any of the sequences set forth in SEQ ID NOs: 1, 2 or 3, including analogues or derivatives thereof, when joined with a leader sequence, including, but not limited to the sequence set forth in SEQ ID NO: 4, will be referred to herein as either a "synthetic peptide" or "synthetic peptides." Rigid molecules that mimic the three dimensional structure of these synthetic peptides are called peptidomimetics and are also included within the scope of this invention. Alpha helix stabilizing amino acid residues at either or both the amino or carboxyl terminal ends of the p53 peptide may be added to stabilize the alpha helical conformation which is known to be the conformation of this region of the p53 protein when it binds to the MDM-2 protein. Examples of alpha helical stabilizing amino acids include Leu, Glu (especially on the amino terminal of the helix), Met and Phe.

Amino acid insertional derivatives of the peptides of the present invention include amino and/or carboxyl terminal fusions as well as intra-sequence insertions of single or multiple amino acids. Insertional amino acid sequence variants are those in which one or more amino acid residues are introduced into a predetermined site in a subject peptide although random insertion is also possible with suitable screening of the resulting product. Deletional variants may be made by removing one or more amino acids from the sequence of a subject peptide. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
|---|---|
| Ala (A) | Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Pro |
| His (H) | Asn; Gln |
| Ile (I) | Leu; Val |

TABLE 1-continued

Suitable residues for amino acid substitutions

| Original Residue | Exemplary Substitutions |
|---|---|
| Leu (L) | Ile; Val |
| Lys (K) | Arg; Gln; Glu |
| Met (M) | Leu; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

When the synthetic peptide is derivatised by amino acid substitution, the amino acids are generally replaced by other amino acids having like properties such as hydrophobicity, hydrophilicity, electronegativety, bulky side chains and the like. As used herein, the terms "derivative", "analogue", "fragment", "portion" and "like molecule" refer to a subject peptide having the amino acid sequence as set forth in SEQ ID NOs: 1, 2, 3, or 4, having an amino acid substitution, insertion, addition, or deletion, as long as said derivative, analogue, fragment, portion, or like molecule retains the ability to enter and selectively kill transformed or neoplastic cells.

The synthetic peptides of the present invention may be synthesized by a number of known techniques. For example, the peptides may be prepared using the solid-phase technique initially described by Merrifield (1963) in J. *Am. Chem. Soc.* 85:2149-2154. Other peptide synthesis techniques may be found in M. Bodanszky et al. *Peptide Synthesis*, John Wiley and Sons, 2d Ed., (1976) and other references readily available to those skilled in the art. A summary of polypeptide synthesis techniques may be found in J. Sturart and J. S. Young, *Solid Phase Peptide Synthesis*, Pierce Chemical Company, Rockford, Ill., (1984). Peptides may also be synthesized by solution methods as described in *The Proteins*, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, *Protective Groups in Organic Chemistry*, Plenum Press, New York, N.Y. (1973). The peptides of the present invention may also be prepared by chemical or enzymatic cleavage from larger portions of the p53 protein or from the full length p53 protein. Likewise, leader sequences for use in the synthetic peptides of the present invention may be prepared by chemical or enzymatic cleavage from larger portions or the full length proteins from which such leader sequences are derived.

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide selectively lethal to malignant and transformed mammalian cells. The present invention also contemplates a deoxyribonucleic acid (DNA) molecule that defines a gene coding for, i.e., capable of expressing a subject peptide or a chimeric peptide from which a peptide of the present invention may be enzymatically or chemically cleaved.

When applied to cells grown in culture, synthetic peptides are selectively lethal to malignant or transformed cells, resulting in dose dependent reduction in cell number. The effect is observable generally within two to three and at most 48 hours. A line of rat pancreatic acinar cells (BMRPA.430) grown in culture was transformed with K-ras. The normal cell line displays the architecture typical of pancreatic acinar cells; the transformed cells (TUC-3) lack the differentiated morphology of acinar cells, appearing as typical pancreatic cancer cells. When BMRPA.430 cells were treated with a synthetic peptide with the primary structure of SEQ ID NO:1 coupled to leader sequence SEQ ID NO:4, at a dosage of 50 µg/ml, the cells were not affected. However, when TUC-3 cells were treated with a peptide with the primary structure of SEQ ID NO:1 coupled to leader sequence SEQ ID NO:4, at a dosage of 100 µg/ml, they died within three to four days. Similar results were obtained when the same experiment was performed but SEQ ID NO:1 was substituted with either SEQ ID NO:2, or SEQ ID NO:3. Additionally, transformed and malignant cell death was observed in human breast carcinoma cell lines and Melanoma and HeLa cells treated with a synthetic peptide with the primary structure of SEQ ID NO:1 coupled to leader sequence SEQ ID NO:4, at a dosage of 100 µg/ml. In contrast, the same synthetic peptide at the same dosage had no effect on non-malignant and non-transformed human breast or fibroblast cell lines.

When the leader sequence set forth in SEQ ID NO:4 was positioned at the carboxy terminal end of PNC29, a control protein having the following amino acid sequence: MPFST-GKRIMLGE (SEQ ID NO: 25), there was no effect on malignant or normal cells.

Additionally, the peptide having the amino acid sequence as set forth in SEQ ID NO:3 fused at the carboxy terminal end to the leader peptide set forth in SEQ ID NO:4, has no effect on the ability of human stem cells to differentiate into hematopoietic cell lines in the presence of growth factors. This indicates that this peptide will not be injurious to bone marrow cells when administered as a chemotherapeutic agent. See Kanovsky et al., (Oct. 23, 2001) *Proc. Nat. Acad. Sci. USA* 98(22); 12438-12443, the disclosure of which is incorporated by reference herein as if fully set forth.

When cultured cancer cells were treated with a peptide with the primary structure of SEQ ID NO:1 without a leader sequence attached, at a dosage of 100 µg/ml, the cells were unaffected. Similarly, when cultured cancer cells were treated with leader sequence SEQ ID NO:4, the presently preferred leader sequence, at the same dosage, the cell were also unaffected. These results indicate that the leader sequence of the synthetic peptide allows the synthetic peptide to cross the cellular membranes of treated cells and that the effect of the synthetic peptide is necessarily intracellular.

In order to determine whether the synthetic peptides acted by interfering with the binding of the p53 protein and the MDM-2 protein, the synthetic peptides were tested on transformed colorectal adenocarcinoma cells that had been rendered incapable of making the p53 protein by homozygous deletion. Surprisingly, the synthetic peptides selectively killed the transformed cells, but had no effect on the normal cells. These results indicate that the mechanism of action appears to be independent of the p53 protein binding to the MDM-2 protein, as the p53 peptide selectively kills transformed cells that do not produce the p53 protein at all. These results indicate that interference with binding of the p53 protein to the MDM-2 protein may not be the mechanism by which synthetic peptides cause selective death of malignant and transformed cells. Although the synthetic peptides disclosed herein, their derivatives, analogues, and peptidomimetic molecules are useful in the treatment of neoplastic disease such as cancer, the mechanism for action on transformed and malignant cells has not been discovered.

The peptides of the present invention are effective against neoplastic cells in vivo. For example, mice having been xenotransplanted with the pancreatic carcinoma cells BMRPA1.TUC-3 and having developed tumor size of about 3-6 mm, have the size of such tumors drastically reduced after administration of a subject synthetic peptide, e.g., a peptide having the amino acid sequence as set forth in SEQ ID NO:3 fused to a leader sequence at the carboxy terminal end.

Consistent with the observed properties of the peptides of the invention, the subject peptides may be used to selectively kill neoplastic or malignant cells, i.e., cancer cells in animals, preferentially humans. The synthetic peptides of the present invention are thus administered in an effective amount to kill neoplastic cells in a subject animal or human.

The synthetic peptides of the present invention may be administered preferably to a human patient as a pharmaceutical composition containing a therapeutically effective dose of at least one synthetic peptide according to the present invention together with a pharmaceutical acceptable carrier. The term "therapeutically effective amount" or "pharmaceutically effective amount" means the dose needed to produce in an individual, suppressed growth including selective killing of neoplastic or malignant cells, i.e., cancer cells.

Preferably, compositions containing one or more of the synthetic peptides of the present invention are administered intravenously for the purpose of selectively killing neoplastic cells, and therefore, treating neoplastic or malignant disease such as cancer. Examples of different cancers which may be effectively treated using one or more the peptides of the present invention include but are not limited to: breast cancer, prostate cancer, lung cancer, cervical cancer, colon cancer, melanoma, pancreatic cancer and all solid tissue tumors (epithelial cell tumors) and cancers of the blood including but not limited to lymphomas and leukemias.

Administration of the synthetic peptides of the present invention may be by oral, intravenous, intranasal, suppository, intraperitoneal, intramuscular, intradermal or subcutaneous administration or by infusion or implantation. When administered in such manner, the synthetic peptides of the present invention may be combined with other ingredients, such as carriers and/or adjuvants. There are no limitations on the nature of the other ingredients, except that they must be pharmaceutically acceptable, efficacious for their intended administration, cannot degrade the activity of the active ingredients of the compositions, and cannot impede importation of a subject peptide into a cell. The peptide compositions may also be impregnated into transdermal patches, or contained in subcutaneous inserts, preferably in a liquid or semi-liquid form which patch or insert time-releases therapeutically effective amounts of one or more of the subject synthetic peptides.

The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents. Examples of such agents include paraben, chlorbutanol, phenol, sorbic acid or thimerosal. Isotonic agents such as sugars or sodium chloride may also be incorporated into the subject compositions.

As used herein, a "pharmaceutically acceptable carrier" includes any and all solvents, dispersion media, coatings, antibacterial and antifungal agents, isotonic agents and the like. The use of such media and agents are well-known in the art.

Production of sterile injectable solutions containing the subject synthetic peptides is accomplished by incorporating one or more of the subject synthetic peptides described hereinabove in the required amount in the appropriate solvent with one or more of the various ingredients enumerated above, as required, followed by sterilization, preferably filter sterilization. In order to obtain a sterile powder, the above solutions are vacuum-dried or freeze-dried as necessary.

Inert diluents and/or assimilable edible carriers and the like may be part of the pharmaceutical compositions when the peptides are administered orally. The pharmaceutical compositions may be in hard or soft shell gelatin capsules, be compressed into tablets, or may be in an elixir, suspension, syrup or the like.

The subject synthetic peptides are thus compounded for convenient and effective administration in pharmaceutically effective amounts with a suitable pharmaceutically acceptable carrier in a therapeutically effective dosage. Examples of a pharmaceutically effective amount includes peptide concentrations in the range from about at least about 25 ug/ml to at least about 300 ug/ml.

A precise therapeutically effective amount of synthetic peptide to be used in the methods of the invention applied to humans cannot be stated due to variations in stage of neoplastic disease, tumor size and aggressiveness, the presence or extent of metastasis, etc. In addition, an individual's weight, gender, and overall health must be considered and will effect dosage. It can be generally stated, however, that the synthetic peptides of the present invention be administered in an amount of at least about 10 mg per dose, more preferably in an amount up to about 1000 mg per dose. Since the peptide compositions of the present invention will eventually be cleared from the bloodstream, re-administration of the pharmaceutical compositions is indicated and preferred.

The synthetic peptides of the present invention may be administered in a manner compatible with the dosage formulation and in such an amount as will be therapeutically effective. Systemic dosages depend on the age, weight, and condition of the patient and the administration route. An exemplary suitable dose for the administration to adult humans ranges from about 0.1 to about 20 mg per kilogram of body weight. Preferably, the dose is from about 0.1 to about 10 mg per kilogram of body weight.

In accordance with the present invention, there is also provided a method of treating neoplastic disease. The method comprises administering to a subject in need of such treatment, a therapeutically effective amount of a synthetic peptide hereinbefore described, including analogs and derivatives thereof. Thus for example, in one embodiment, an effective amount of a peptide comprising at least about six contiguous amino acids as set forth in SEQ ID NO:1 or an analog or derivative thereof fused on its carboxy terminal end to a leader sequence may be administered to a subject. In another embodiment, an effective amount of a peptide comprising at least from about eight (8) to at least about ten (10) contiguous amino acids as set forth in SEQ ID NO:1 or an analog or derivative thereof, fused on its carboxy terminal end to a leader sequence, may be administered to a subject. For example, an effective amount of a peptide having the amino acid sequence as set forth in SEQ ID NO:1 or an analog or derivative thereof, fused on its carboxy terminal end to a leader sequence may be administered to a subject. An effective amount of a peptide having the amino acid sequence as set forth in SEQ ID NO:2 or an analog or derivative thereof, fused on its carboxy terminal end to a leader sequence may also be administered to a subject. In still another embodiment, an effective amount of a peptide having the amino acid sequence set forth in SEQ ID NO:3 or an analog or derivative thereof, fused on its carboxy terminal end to a leader sequence may be administered to a subject. In accordance with a method of treatment, a mixture of synthetic peptides may be administered. Thus, for example, in addition to administering one of the peptides, or analogs or derivatives thereof hereinbefore described in an effective amount, mixtures of two or more peptides or analogs or derivatives hereinbefore described may be administered to a subject.

there was no cell death, and approximately half of the cells were seen to form acini and exhibited the untransformed morphological phenotype. The same phenomena were observed at 50 μg/ml, and at 25 μg/ml significantly fewer cells were seen to revert. In contrast, when the leader sequence was attached to the carboxyl terminal end of the peptide (PNC28 in Table 2), at dosages of 50 and 100 μg/ml. 100% cell death occurred in about 4 days.

These results show that the leader sequence is preferentially added to the carboxyl terminal end of the MDM-2 portion of the p53 peptide to enable the peptide to cross the cell membrane and specifically kill malignant cells. In Table 2, the leader sequence is KKWKMRRNQFWVKVQRG (SEQ ED NO:4).

TABLE 2

| NAME | p53 seq. | PEPTIDE | EFFECT |
|---|---|---|---|
| 1. PNC 21 | 12-20 | (PPLSQETFS) (SEQ ID NO: 2)-Leader | Cytotoxic |
| 2. PNC 27 | 12-26 | (PPLSQETFSDLWKLL) (SEQ ID NO: 1)-Leader | Cytotoxic |
| 3. PNC 28 | 17-26 | (ETFSDLWKLL) (SEQ ID NO: 3)-Leader | Cytotoxic |
| 4. PNC 28' | 17-26 | Leader (ETFSDLWKLL) (SEQ ID NO: 3) | No cell death and reversion |

The following examples further illustrate the invention and are not meant to limit the scope thereof.

Example I

The following experiment was performed to compare effectiveness of subject peptides having the leader sequence attached to the amino terminal end. As described supra, peptides synthesized with a leader sequence on the carboxyl terminal promoted α-helix formation in the peptide, which is the active conformation of the p53 part of this peptide when bound to MDM-2. As described supra, subject peptides having the amino acid sequences as set forth in SEQ ID NOs:1, 2, and 3 are strongly toxic to a wide variety of human cancer cells, including those that are homozygously p53 gene-deleted. An α-helix probability profile for each peptide having the sequences set forth in SEQ ID NOs:1-3 was performed using two different methods, one using helix probabilities from the protein database (Karplus, K. et al., (1998) *Bioinformatics* 14:846-856), and the other using the Ising model based on helix nucleation (σ) and growth (s), equilibrium constants determined experimentally from block copolymers for each of the twenty naturally occurring L amino acids, modified by inclusion of the effects of charges on these parameters as described in Vasquez, M., et al. (1987) *Biopolymers* 26:351-372 and Vasquez, M., et al., (1987) *Biopolymers* 26:373-393. Probability profiles indicated that if the leader sequence is on the amino terminal end, even though the peptide still transverses the cell membrane, the α-helical content is much lower.

The peptide having the sequence set forth in SEQ ID NO:3 was synthesized by solid phase synthesis with the leader sequence attached to the amino terminal end. This peptide is labeled PNC28' in Table 2 below. The PNC28' peptide was incubated with transformed pancreatic cancer (TUC-3) cells at three different concentrations, i.e., 25, 50 and 100 μg/ml. After two weeks of incubation, at the highest dose of peptide, These results indicate the uniqueness of the subject peptides. i.e., the leader or cluster of positively charged residues must be placed at the carboxy terminal end of any effector peptide for cancer cell toxicity.

Example II

Nu/Nu mice (Harlan Laboratories, Indianapolis, Ind., n=10) and weighing 20-22 g, were xenotransplanted subcutaneously (s.c.) with live pancreatic carcinoma cells BMRPA1.TUC-3 ($1 \times 10^6$ cells/mouse) in the left hind region. Tumors were allowed to develop and grow and during daily examinations it was observed that all mice developed tumors with very similar growth rates.

After 12 days the tumors had reached sizes of 3 to 6 mm diameter and the mice were separated into two groups of 5 mice each. Each group was implanted s.c. with Alzet® osmotic pumps to deliver in a constant rate and over a defined period of 14 days a total volume of 0.095 ml volume of normal saline containing the respective peptide at a concentration of 20 mg/mouse. One group of mice received PNC-28 (the peptide having the amino acid set forth in SEQ ID NO:3) fused at its carboxy terminal end to the penetratin leader sequence (SEQ ID NO:4) and the other group of mice received PNC-29, a control peptide of similar size, having the following amino acid sequence: MPFSTGKRIMLGE (SEQ ID NO: 25). The pumps were filled according to the manufacturers guidelines and under sterile conditions The pumps were implanted s.c. on the left flank of the anaesthetized mice by creating a pocket underneath the mouse skin into which the tiny pumps were inserted. Each pocket was closed with a simple suture. From their inside chamber the pumps delivered continuously 0.25 μl/hr into each mouse. The mice were observed until they had recovered from the surgery when they were returned to the isolation ward of the animal facility. Since the animals were Nu/Nu mice and, thus, immunocompromised they are highly susceptible when exposed to pathogens. Surgery and all preceding and post-surgical treatments were therefore performed in a sterile hood environment.

As shown clearly in FIG. 1, PNC-28 within a 48 to 72 hr period of delivery into the mouse effectively arrests tumor growth. In contrast, the control peptide PNC-29 had no effect on normal or tumor cells. In PNC29-treated mice, tumors kept growing at a continuous rate resulting in tumors of 10 to 16 mm diameter over the 2-week treatment and follow-up period when the pumps cease to release any more peptide solution. Statistical analyses of the measurement of tumor size in both groups of mice has produced a significance between them of $p<0.001$.

Example III

Using the same methodology of Example II, pumps were started at the same time as live pancreatic carcinoma cells BMRPA1.TUC-3 ($1\times10^6$ cells/mouse) were xenotransplanted into mice (n=10). Five mice were administered PNC28 and 5 mice were not treated at all (sham treated). Results are tabulated below.

TABLE 3

| Treatment | 7 Days | 14 Days Tumor Size | 21 Days |
|---|---|---|---|
| Sham treated | 4.8 ± 1.8 | 11.7 ± 2.3 | 14.8 ± 3.6 |
| PNC-28 treated | 3 ± .6 | 3.1 ± .9 | 4.4 ± .8 |

Example IV

Using the same methodology as described in Example II, live pancreatic carcinoma cells BMRPA1.TUC-3 ($1\times10^6$ cells/mouse) were transplanted to the peritoneal cavity of five mice. Pumps were placed in the right shoulder region at the same time of tumor cell transplantation. In all five mice, there were no visible tumors after three weeks.

The foregoing specification, and the experimental results reported therein are illustrative and are not limitations of the scope of applicant's invention. Those skilled in the art will appreciate that various modifications can be made without departing from applicant's invention.

---

What is claimed is:

1. A composition comprising a peptide, the peptide consisting of the amino acid sequence: PPLSQETFSDLWKLL (SEQ ID NO:1) fused to a membrane-penetrating leader sequence.

2. A composition comprising a peptide, the peptide consisting of the amino acid sequence: PPLSQETFS (SEQ ID NO:2) fused to a membrane penetrating leader sequence.

3. A composition comprising a peptide, the peptide consisting of the amino acid sequence: ETFSDLWKLL (SEQ ED NO:3) fused to a membrane penetrating leader sequence.

4. A composition comprising at least one peptide consisting of the amino acid sequence: PPLSQETFSDLWKLL (SEQ ID NO:1), PPLSQETFS (SEQ ID NO:2), or ETFSDLWKLL (SEQ ID NO:3), said peptide fused to a membrane penetrating leader sequence.

5. The composition of any one of claims 1-4 wherein the membrane-penetrating leader sequence comprises the amino acid sequence: KKWKMRRNQFWVKVQRG (SEQ ID NO:4).

6. The composition according to any one of claims 1-4 which is a pharmaceutical composition, wherein the peptide is admixed with a pharmaceutically acceptable carrier.

7. The composition according to claim 5 which is a pharmaceutical composition, wherein the peptide is admixed with a pharmaceutically acceptable carrier.

8. A method of treating neoplastic disease in a subject, said method comprising administering to the subject, a therapeutically effective amount of a composition comprising at least one peptide consisting of the amino acid sequence: PPLSQETFSDLWKLL (SEQ ID NO:1), PPLSQETFS (SEQ ID NO:2), or ETFSDLWKLL (SEQ ID NO:3), said peptide fused to a membrane penetrating leader sequence.

9. A method of treating neoplastic disease in a subject, said method comprising administering to the subject, a therapeutically effective amount of the composition of any one of claims 1-4.

10. The method of claim 8 wherein the composition is a pharmaceutical composition comprising the peptide admixed with a pharmaceutically acceptable carrier.

11. The method of claim 8 wherein the membrane-penetrating leader sequence comprises the amino acid sequence: KKWKMRRNQFWVKVQRG (SEQ ID NO:4).

12. The method of claim 9 wherein the composition is a pharmaceutical composition comprising the peptide admixed with a pharmaceutically acceptable carrier.

13. The method of claim 9 wherein the membrane-penetrating leader sequence comprises the amino acid sequence: KKWKMRRNQFWVKVQRG (SEQ ID NO:4).

* * * * *

SEQUENCE LISTING

```
<160> NUMBER OF SEQ ID NOS: 27

<210> SEQ ID NO 1
<211> LENGTH: 15
<212> TYPE: PRT
<213> ORGANISM: Artificial Sequence
<220> FEATURE:
<223> OTHER INFORMATION: peptide; amino acid residues 12-26 of human p53
      protein

<400> SEQUENCE: 1

Pro Pro Leu Ser Gln Glu Thr Phe Ser Asp Leu Trp Lys Leu Leu
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: peptide; amino acid residues 12-20 of human p53
      protein

<400> SEQUENCE: 2

Pro Pro Leu Ser Gln Glu Thr Phe Ser
1               5

<210> SEQ ID NO 3
<211> LENGTH: 10
<212> TYPE: PRT
<213> ORGANISM: Artificial Sequence
<220> FEATURE:
<223> OTHER INFORMATION: peptide; amino acid residues 17-26 of human p53
      protein

<400> SEQUENCE: 3

Glu Thr Phe Ser Asp Leu Trp Lys Leu Leu
1               5                   10

<210> SEQ ID NO 4
<211> LENGTH: 17
<212> TYPE: PRT
```

```
<213> ORGANISM: Artificial Sequence
<220> FEATURE:
<223> OTHER INFORMATION: peptide; penetratin leader sequence from
      antennapedia

<400> SEQUENCE: 4

Lys Lys Trp Lys Met Arg Arg Asn Gln Phe Trp Val Lys Val Gln Arg
1               5                   10                  15

Gly

<210> SEQ ID NO 5
<211> LENGTH: 14
<212> TYPE: PRT
<213> ORGANISM: Artificial Sequence
<220> FEATURE:
<223> OTHER INFORMATION: peptide; HIV-1 TAT membrane penetrating leader
      sequence

<400> SEQUENCE: 5

Tyr Gly Arg Lys Lys Arg Arg Gln Arg Arg Pro Pro Gln
1               5                   10

<210> SEQ ID NO 6
<211> LENGTH: 13
<212> TYPE: PRT
<213> ORGANISM: Artificial Sequence
<220> FEATURE:
<223> OTHER INFORMATION: peptide; D-TAT membrane penetrating leader
      sequence

<400> SEQUENCE: 6

Gly Arg Lys Lys Arg Arg Gln Arg Arg Arg Pro Pro Gln
1               5                   10

<210> SEQ ID NO 7
<211> LENGTH: 13
<212> TYPE: PRT
<213> ORGANISM: Artificial Sequence
<220> FEATURE:
<223> OTHER INFORMATION: peptide; R-TAT membrane penetrating leader
      sequence

<400> SEQUENCE: 7

Gly Arg Arg Arg Arg Arg Arg Arg Arg Arg Pro Pro Gln
1               5                   10

<210> SEQ ID NO 8
<211> LENGTH: 7
<212> TYPE: PRT
<213> ORGANISM: Artificial Sequence
<220> FEATURE:
<223> OTHER INFORMATION: peptide; SV40-NLS membrane penetrating leader
      sequence

<400> SEQUENCE: 8

Pro Lys Lys Lys Arg Lys Val
1               5

<210> SEQ ID NO 9
<211> LENGTH: 16
<212> TYPE: PRT
<213> ORGANISM: Artificial Sequence
<220> FEATURE:
<223> OTHER INFORMATION: peptide; nucleoplasm-NLS membrane penetrating
      leader sequence

<400> SEQUENCE: 9
```

```
Lys Arg Pro Ala Ala Ile Lys Lys Ala Gly Gln Ala Lys Lys Lys Lys
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: peptide; HIV REV membrane penetrating leader
      sequence

<400> SEQUENCE: 10

Thr Arg Gln Ala Arg Arg Asn Arg Arg Arg Trp Arg Glu Arg Gln
1               5                   10                  15

Arg

<210> SEQ ID NO 11
<211> LENGTH: 15
<212> TYPE: PRT
<213> ORGANISM: Artificial Sequence
<220> FEATURE:
<223> OTHER INFORMATION: peptide; FHV coat protein membrane penetrating
      leader sequence

<400> SEQUENCE: 11

Arg Arg Arg Arg Asn Arg Thr Arg Arg Asn Arg Arg Arg Val Arg
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: peptide; BMV GAG membrane penetrating leader
      sequence

<400> SEQUENCE: 12

Lys Met Thr Arg Ala Gln Arg Arg Ala Ala Ala Arg Arg Asn Arg Trp
1               5                   10                  15

Thr Ala Arg

<210> SEQ ID NO 13
<211> LENGTH: 13
<212> TYPE: PRT
<213> ORGANISM: Artificial Sequence
<220> FEATURE:
<223> OTHER INFORMATION: peptide; HTLV-II REX membrane penetrating
      leader sequence

<400> SEQUENCE: 13

Thr Arg Arg Gln Arg Thr Arg Arg Ala Arg Arg Asn Arg
1               5                   10

<210> SEQ ID NO 14
<211> LENGTH: 19
<212> TYPE: PRT
<213> ORGANISM: Artificial Sequence
<220> FEATURE:
<223> OTHER INFORMATION: peptide; CCMV GAG membrane penetrating leader
      sequence

<400> SEQUENCE: 14

Lys Leu Thr Arg Ala Gln Arg Arg Ala Ala Ala Arg Lys Asn Lys Arg
1               5                   10                  15

Asn Thr Arg
```

```
<210> SEQ ID NO 15
<211> LENGTH: 17
<212> TYPE: PRT
<213> ORGANISM: Artificial Sequence
<220> FEATURE:
<223> OTHER INFORMATION: peptide; P22 N membrane penetrating leader
      sequence

<400> SEQUENCE: 15

Asn Ala Lys Thr Arg Arg His Glu Arg Arg Arg Lys Leu Ala Ile Glu
1               5                   10                  15

Arg

<210> SEQ ID NO 16
<211> LENGTH: 22
<212> TYPE: PRT
<213> ORGANISM: Artificial Sequence
<220> FEATURE:
<223> OTHER INFORMATION: peptide; LAMBDA N membrane penetrating leader
      sequence

<400> SEQUENCE: 16

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 17
<211> LENGTH: 18
<212> TYPE: PRT
<213> ORGANISM: Artificial Sequence
<220> FEATURE:
<223> OTHER INFORMATION: peptide; Phi N membrane penetrating leader
      sequence

<400> SEQUENCE: 17

Thr Ala Lys Thr Arg Tyr Lys Ala Arg Arg Ala Glu Leu Ile Ala Glu
1               5                   10                  15

Arg Arg

<210> SEQ ID NO 18
<211> LENGTH: 16
<212> TYPE: PRT
<213> ORGANISM: Artificial Sequence
<220> FEATURE:
<223> OTHER INFORMATION: peptide; Yeast PRP6 membrane penetrating leader
      sequence

<400> SEQUENCE: 18

Thr Arg Arg Asn Lys Arg Asn Arg Ile Gln Glu Gln Leu Asn Arg Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: peptide; Human U2AF membrane penetrating leader
      sequence

<400> SEQUENCE: 19

Ser Gln Met Thr Arg Gln Ala Arg Arg Leu Tyr Val
1               5                   10

<210> SEQ ID NO 20
```

```
<211> LENGTH: 26
<212> TYPE: PRT
<213> ORGANISM: Artificial Sequence
<220> FEATURE:
<223> OTHER INFORMATION: peptide; Human C-FOS membrane penetrating
      leader sequence

<400> SEQUENCE: 20

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 21
<211> LENGTH: 28
<212> TYPE: PRT
<213> ORGANISM: Artificial Sequence
<220> FEATURE:
<223> OTHER INFORMATION: peptide; Human C-JUN membrane penetrating
      leader sequence

<400> SEQUENCE: 21

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 22
<211> LENGTH: 22
<212> TYPE: PRT
<213> ORGANISM: Artificial Sequence
<220> FEATURE:
<223> OTHER INFORMATION: peptide; Yeast GCN4 membrane penetrating leader
      sequence

<400> SEQUENCE: 22

Lys Arg Ala Arg Asn Thr Glu Ala Ala Arg Arg Ser Arg Ala Arg Lys
1               5                   10                  15

Leu Gln Arg Met Lys Gln
            20

<210> SEQ ID NO 23
<211> LENGTH: 18
<212> TYPE: PRT
<213> ORGANISM: Artificial Sequence
<220> FEATURE:
<223> OTHER INFORMATION: peptide; membrane penetrating leader sequence

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 18
<212> TYPE: PRT
<213> ORGANISM: Artificial Sequence
<220> FEATURE:
<223> OTHER INFORMATION: peptide; p-vec membrane penetrating leader
      sequence

<400> SEQUENCE: 24

Leu Leu Ile Ile Leu Arg Arg Arg Ile Arg Lys Gln Ala Lys Ala His
1               5                   10                  15

Ser Lys
```

```
<210> SEQ ID NO 25
<211> LENGTH: 13
<212> TYPE: PRT
<213> ORGANISM: Artificial Sequence
<220> FEATURE:
<223> OTHER INFORMATION: peptide; used as a control

<400> SEQUENCE: 25

Met Pro Phe Ser Thr Gly Lys Arg Ile Met Leu Gly Glu
1               5                   10

<210> SEQ ID NO 26
<211> LENGTH: 8
<212> TYPE: PRT
<213> ORGANISM: Artificial Sequence
<220> FEATURE:
<223> OTHER INFORMATION: peptide; Arg(8) membrane penetrating leader
      sequence

<400> SEQUENCE: 26

Arg Arg Arg Arg Arg Arg Arg Arg
1               5

<210> SEQ ID NO 27
<211> LENGTH: 16
<212> TYPE: PRT
<213> ORGANISM: Artificial Sequence
<220> FEATURE:
<223> OTHER INFORMATION: peptide; poly-R membrane penetrating leader
      sequence
<220> FEATURE:
<221> NAME/KEY: MISC_FEATURE
<222> LOCATION: (5)..(16)
<223> OTHER INFORMATION: Xaa=Arg and may be present or absent

<400> SEQUENCE: 27

Arg Arg Arg Arg Xaa Xaa Xaa Xaa Xaa Xaa Xaa Xaa Xaa Xaa Xaa Xaa
1               5                   10                  15
```